(12) United States Patent
Magota et al.

(10) Patent No.: US 6,171,828 B1
(45) Date of Patent: Jan. 9, 2001

(54) METHOD FOR CULTURING MICROORGANISMS HAVING A METHANOL METABOLIC PATHWAY

(75) Inventors: Koji Magota; Tomohiro Rogi, both of Takatsuki; Yasuyoshi Sakai, Ohtsu; Nobuo Kato, Kameoka, all of (JP)

(73) Assignee: Suntory Limited, Osaka (JP)

( * ) Notice: Under 35 U.S.C. 154(b), the term of this patent shall be extended for 0 days.

(21) Appl. No.: 08/811,024

(22) Filed: Mar. 4, 1997

(30) Foreign Application Priority Data

Mar. 4, 1996 (JP) .................................................. 8-070899

(51) Int. Cl.[7] ....................................................... C12P 1/02
(52) U.S. Cl. ..................... 435/69.9; 435/254.22; 435/255.4; 435/255.5; 435/255.6; 435/224
(58) Field of Search .............................. 435/69.9, 254.22, 435/255.4, 226, 255.5, 255.6, 224; 530/350

(56) References Cited

U.S. PATENT DOCUMENTS

| | | | |
|---|---|---|---|
| 4,342,832 | * | 8/1982 | Goeddel et al. ...................... 435/172 |
| 5,612,198 | * | 3/1997 | Brierley et al. ...................... 435/69.9 |

FOREIGN PATENT DOCUMENTS

| | | | |
|---|---|---|---|
| 0 510 693 | * | 10/1992 | (EP) . |
| 0 510 693 A2 | * | 10/1992 | (EP) . |
| 0 558 024 | | 9/1993 | (EP) . |
| 0 794 256 | * | 9/1997 | (EP) . |
| 4-27384 | * | 1/1992 | (JP) . |
| WO 92/13951 | * | 8/1992 | (WO) . |
| WO 95/21928 | * | 8/1995 | (WO) . |

OTHER PUBLICATIONS

Callard et al. (1994) The Cytokine FactsBook, Academic Press Harcourt Brace & Company: London, pp. 233 and 235.*
Brenner et al, "Structural and enzymatic characterization of a purified prohormone–processing enzyme: Secreted, soluble Kex2 protease", Proc. Natl. Acad. Sci., 89:922–926, 1992.*
Gellisen et al, "Heterologous Gene Expression in *Hansenula Polymorpha*: Efficient Secretion of Glucoamylase", Bio/Technology, 9:291–295, 1991.*
European Search Reported dated May 8, 1998.*

* cited by examiner

*Primary Examiner*—Lorraine Spector
(74) *Attorney, Agent, or Firm*—Burns, Doane, Swecker & Mathis, L.L.P.

(57) ABSTRACT

The present invention discloses a method for culturing microorganisms having a methanol metabolic pathway in which an expression unit is introduced that comprises a target gene linked downstream from a promoter that can be induced by methanol; wherein, during the culturing period, and including the period during which methanol is continuously or periodically added, the rate of addition is adjusted to a rate equal to or less than the maximum methanol consumption rate of said microorganisms.

28 Claims, 7 Drawing Sheets

Fig. 1b

PRIMERS

NKEX2: 5' GCGGCCGCTTAAACATCCCGTTTGTAAAAGAGA 3'
        <u>Not I</u>

KM088: 5' TAAGTCGACTTAAGGATGGTACTCGCAGTAGTCG 3'
        <u>Sal I</u>   ProAspThrSerAlaThrThr

▦ : GENE CODING FOR Kex2 PROTEASE (814 AMINO ACID RESIDUES)

▧ : REGION CODING FOR A REGION RICH IN HYDROPHOBIC AMINO ACID RESIDUES

▨ : REGION CODING FOR A REGION RICH IN SERINE AND THREONINE AMINO ACID RESIDUES

▦ : REGION HIGHLY SIMILAR TO SUBTILISIN

THOSE AMINO ACIDS ENCODED BY DNA COMPLEMENTARY TO KM088 (CORRESPONDING TO AMINO ACIDS 654-660 OF Kex2 PROTEASE) ARE SHOWN BELOW THE BASE SEQUENCE OF KM088.

* AMOUNT OF METHANOL ADDED PER LITER
OF CULTURE MEDIUM PER HOUR

Fig. 6

10% SDS-PAGE USING 5 μl OF CULTURE SUPERNATANT/LANC

CULTURING TIME (h)  0  6  12  18  24  30  36  42  48

← Kex2

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 35 base pairs
      (B) TYPE: nucleic acid
      (C) STRANDEDNESS: single
      (D) TOPOLOGY: linear    (ii) MOLECULE TYPE: other nucleic acid
      (A) DESCRIPTION: /desc = "synthetic DNA"

(xi) SEQUENCE DESCRIPTION: SEQ ID NO:1:

GCGGCCGCTT AAACATCCCG TTTTGTAAAA AGAGA                              35

(2) INFORMATION FOR SEQ ID NO:2:

(i) SEQUENCE CHARACTERISTICS:
      (A) LENGTH: 35 base pairs
      (B) TYPE: nucleic acid
      (C) STRANDEDNESS: single
      (D) TOPOLOGY: linear    (ii) MOLECULE TYPE: other nucleic acid
      (A) DESCRIPTION: /desc = "synthetic DNA"

(xi) SEQUENCE DESCRIPTION: SEQ ID NO:2:

TAAGTCGACT TAAGGATCGG TACTCGCAGT AGTCG                              35

METHOD FOR CULTURING MICROORGANISMS HAVING A METHANOL METABOLIC PATHWAY

BACKGROUND OF INVENTION

1. Field of Invention

The present invention relates to a method for culturing microorganisms having a methanol metabolic pathway into which has been introduced an expression unit in which a target gene is linked downstream to a promoter able to be induced by methanol, said method enabling the target gene product to be produced efficiently.

2. Related Art

The production of polypeptides and other gene products using microorganisms as hosts has basically become possible due to the advances made in recombinant DNA technology. Polypeptide production is performed by introducing an expression unit in which the gene for a target polypeptide is linked downstream to a suitable promoter. Microorganisms such as *E. coli*, yeasts and animal cells are typically used as a host.

Gene expression systems using *E. coli* as the host are the most commonly used systems, and these systems typically provide a high productivity. However, since there are many cases in which the expressed polypeptide forms insoluble inclusion bodies resulting in an insoluble form, the possibility of using this system is largely dependent on the properties of the target polypeptide.

On the other hand, gene expression systems that use animal cells as a host are useful for the purpose of confirming an activity of a gene product and so forth since in many cases the expressed polypeptide retains activity. However, the amount of target polypeptide is typically low, and considerable efforts are required for purification in this case. In addition, since animal cells reproduce slowly and the media used are expensive, culturing requires both considerable time and cost. Moreover, it is also difficult to increase the scale of culturing. Consequently, animal cells are not desirable as a host for industrially obtaining a target polypeptide in large volume.

Yeast cells are eucaryotic cells having endoplasmic reticulum, Golgi apparatus and other cellular components similar to animals cells. They are also known to be able to form and express polypeptides having particularly tertiary structures in polypeptides derived from eucaryotic cells. In addition, they reproduce faster than animal cells and can easily be cultured in large volume. Genetic analyses have been conducted most extensively on *Saccharomyces cerevisiae*, and it is widely used at the laboratory level as a host for gene expression.

However, since it is difficult to grow *Saccharomyces cerevisiae* to a high cell density and yield per culture medium is not high, it is not sufficient for industrial production of the target polypeptide. In order to solve this problem, methylotrophic yeasts such as *Pichia pastoris*, *Hansenula polymorpha* and *Candida boidinii* are used.

For example, Gellissen et al. succeeded in producing 1.4 g of glucoamylase at a cell density of 100 to 130 g dry cell weight per liter of culture medium using a formic dehydrogenase promoter for which expression is induced by methanol and *Hansenula polymorpha* as host (Gellissen et al. BIO/TECHNOLOGY, 9, 291–295, 1991). In addition, Barr et al. succeeded in producing 4 g of human serum albumin per liter of culture medium using an alcohol oxidase promoter for which expression is induced by methanol and *Pichia pastoris* as host (Barr et al. Pharm. Eng., 12(2), 48–51, 1992).

However, the problems described below are still possible even in the case of methods using methylotrophic yeasts. In the case of a yeast having a methanol metabolic pathway in a heterogeneous gene expression system using a yeast represented by the above-mentioned three species of methylotrophic yeasts and a promoter able to be induced by methanol, the methanol in the culture medium rapidly decreases when the yeast is cultured in a medium containing methanol. In this type of culturing, methanol must be supplied as a carbon source in order to simultaneously maintain transcription from the promoter and cell growth.

However, if the methanol concentration in the culture medium is suddenly increased during supply of methanol, the yeast may be killed. In addition, measurement of the methanol concentration in a culture of yeast having a methanol metabolic pathway is generally performed by applying the supernatant to gas chromatography and so forth. In this method, however, in addition to requiring special equipment, since a considerable amount of time is required until methanol concentration can be determined, it has the disadvantage of preventing a rapid judgment from being made regarding the need for replenishment of methanol.

As an example for a method for maintaining methanol concentration in a culture medium for expression of a target gene, a method is used that reduces the methanol consumption rate using a yeast in which the enzyme alcohol oxidase is missing from its metabolic pathway. This method involves growing yeast using glycerol and so forth as a carbon source, and then inducing transcription from a promoter by adding a fixed amount of methanol to the culture medium to express the target gene. Due to the low rate of methanol consumption, it is easy to maintain methanol concentration. Although it is possible to obtain a stable culture, this method has the disadvantage of requiring a long culturing time since culturing is performed separately for a cell growth period and a target gene expression period.

A method is disclosed in WO 95/21928 wherein the methanol concentration in a culture medium is controlled to a constant level in order to express a target gene by culturing a methylotrophic yeast, in which methanol metabolism has been slowed by partially altering enzymes of metabolic pathway, without increasing the number of cells. This method involves measuring a methanol concentration in the air inside the culture tank in a state in which a methanol concentration in the air inside the culture tank reflects the methanol concentration in the culture medium, and then determining the methanol addition rate from those results to control the methanol concentration in the culture medium.

The methanol concentration in a culture medium of methylotrophic yeast deficient for alcohol oxidase gene can be controlled to a constant level by applying this method. However, in order to predict the methanol concentration in the culture medium from the methanol concentration in the air inside the culture tank, it is necessary that both be at equilibrium. In order to achieve this equilibrium, culture conditions including aeration rate, pressure and temperature must be maintained constant, and the methanol concentration in the culture medium must not change suddenly. Due to these restrictions, the above-mentioned method for controlling methanol concentration could only be applied to culturing in the gene expression induction phase after the cells had been grown in advance using a yeast that does not have a methanol metabolic pathway.

On the other hand, in a heterogeneous gene expression system using a promoter capable of being induced with methanol and a microorganism having a methanol metabolic pathway as a host, it is not necessary to isolate the microorganism growth phase and the induction phase for gene expression if the rate of methanol addition and the concentration of methanol in the culture medium are suitably controlled. Consequently, culturing time is shortened which results in the target protein being able to be obtained in a short time. Thus, in the culturing of microorganisms having a methanol metabolic pathway, there is a need to establish a method for maintaining a suitable rate of methanol addition or methanol concentration that satisfies both the production of the target gene product and microorganism growth.

SUMMARY OF THE INVENTION

The present invention provides a method for adjusting the methanol concentration in a culture medium so that induction of a promoter by methanol and growth of a host are able to be performed in parallel in a heterogeneous gene expression system using a methanol-inducible promoter and microorganisms having a methanol metabolic pathway as a host, and a method for culturing a host using that method.

As a result of carefully examining the relationship between the method of methanol addition, the methanol concentration in the culture medium and the amount of dissolved oxygen in the culturing of yeast having a methanol metabolic pathway, the inventors of the present invention found that, if methanol is added periodically when methanol concentration is 0.1% (v/v) or less in a culture in which the amount of dissolved oxygen in the culture medium is controlled to a constant level (e.g. 2 ppm), the amount of dissolved oxygen fluctuates synchronously with the addition cycle of methanol. In addition, it was also found that, when the methanol addition rate is increased in the state in which these periodic fluctuations in the amount of dissolved oxygen are observed, the rate of increase of the amount of dissolved oxygen decreases, and increased the periodic fluctuations in the amount of dissolved oxygen are finally no longer observed, and that when the methanol addition rate is further increased the methanol accumulates in the culture medium and the yeast are killed.

When these periodic fluctuations in the amount of dissolved oxygen are observed, the yeast grows and transcription from a promoter inducible with methanol is induced. Namely, the rate of methanol addition to the culture medium at this time is clearly an addition rate that satisfies both production of the target gene product and yeast growth. Moreover, during the time in which periodic fluctuations are observed, it was confirmed that a faster rate of methanol addition results in faster cell growth and greater production of the target gene product, thus leading to completion of the present invention.

Namely, as a result of being based on the experimental results described above, the present invention provides a method for culturing microorganisms having a methanol metabolic pathway into which an expression unit has been introduced that comprises a target gene linked downstream to a promoter that can be induced by methanol; wherein, during the culturing period including the period during which methanol is continuously or periodically added, the rate of addition is adjusted to a rate equal to or less than the maximum methanol consumption rate of said microorganisms.

DETAILED DESCRIPTION

The maximum methanol consumption rate refers to a rate of methanol consumption by microorganisms for a certain culturing period and under certain conditions of those microorganisms, and under conditions in which methanol concentration does not determine the rate of methanol consumption. Since methanol concentration is maintained at a constant level or gradually increases if methanol is added at a rate equal to or faster than the maximum methanol consumption rate, the rate of methanol addition being equal to or less than the maximum methanol consumption rate of said microorganisms refers to a methanol addition rate at which the methanol concentration in the medium is maintained at a level substantially close to zero, and in practice, at a level at which methanol concentration is maintained at 0.1% (v/v) or less.

In order to obtain a rate of methanol addition as described above, the most typical means in the present invention is the use of a method involving periodic addition of methanol. This periodic addition method refers to the addition of a prescribed amount of methanol at a certain time interval over a certain period of time during culturing. This cycle, namely the time interval, is normally 1 to 20 minutes, and preferably 5 to 10 minutes. As will be described later, according to the new findings of the inventors of the present invention, when the rate of methanol addition, namely the amount of methanol added within a certain unit time (expressed as the number of milliliters of methanol per hour per liter of culture medium in the present invention), is low, the level of the dissolved oxygen concentration in the culture medium fluctuates synchronously with the methanol addition cycle, and the methanol concentration in the culture medium in this case is 0.1% (v/v) and substantially near 0%.

In contrast, in the case where the rate of methanol addition is equal to or greater than the maximum methanol consumption rate of the microorganisms, fluctuations in the level of dissolved oxygen concentration synchronous with the methanol addition cycle substantially do not occur. In this case, methanol at a certain concentration level is observed to accumulate in the culture medium. Thus, by adjusting the rate of methanol addition so that the concentration level of dissolved oxygen in the culture medium fluctuates synchronously with the methanol addition cycle, the methanol addition rate can be adjusted to a rate equal to or less than the maximum rate of methanol consumption by the microorganisms.

However, the above-mentioned method is not the only method for adjusting the rate of methanol addition to a rate equal to or less than the maximum rate of methanol consumption by microorganisms. For example, if certain microorganisms can be cultured under constant conditions in a medium having a constant composition, and similar culture progresses can be reproduced, the methanol addition rate obtained according to the experiment or its changes over time can be applied to another culturing independent of the fluctuations in dissolved oxygen in the culture medium. In this method, the addition of methanol may be performed periodically or continuously.

In addition, in the above-mentioned periodic fluctuations in the concentration level of dissolved oxygen, the rise in the concentration level of dissolved oxygen is a result of depletion caused by consumption of added methanol. If the decrease in the concentration level of dissolved oxygen is taken to be the result of consumption of dissolved oxygen by the consumption of freshly added methanol, the rate of methanol addition can be adjusted to a rate equal to or less than the maximum rate of methanol consumption by microorganisms by repeating the cycle consisting of detecting the increase in the concentration level of dissolved oxygen, adding a constant amount of methanol and adding methanol of next cycle after the concentration level of dissolved oxygen has decreased by the consumption of the added methanol and reincreased by the depletion of methanol.

In the present invention, an inducible promoter refers to a gene promoter that codes for an enzyme involved in methanol metabolism in a microorganism such as yeast, examples of which include a promoter of alcohol oxidase gene (Japanese Unexamined Patent Publication No. 5-344895; Ellis, S.B. et al., Mol. Cell. Biol. 5, 1111–1112, 1985), a promoter of formic dehydrogenase gene (Hollenberg, C. P. et al., EPA No. 0299108, 1988), and a promoter of methanol oxidase gene (Ledeboer, A. M. et al., Nucleic Acids Res. 13, 3063–3082, 1985).

In the present invention, an expression unit refers to an expression vector such as an expression plasmid.

In the present invention, the target gene refers to a gene coding for, for example, a useful protein. Here, useful protein refers to, for example, an enzyme or other physiologically active protein. Various examples of enzymes include Kex 2 protease, prohormone convertase 1/3 (PC1/3), prohormone convertase 2 (PC2), furin, peptide C terminal α-amidase, staphylococcal protease V8, achromobacter protease I (API), placental leucine aminopeptidase, cytoplasmic platelet activating factor acetylhydrase and their derivatives.

In addition, examples of other physiologically active substances include growth hormones, growth hormone releasing hormone, adrenocorticotropic hormone (ACTH) releasing hormone, glucagon, glucagon-like peptide I, glucagon-like peptide II, Interferon α, Interferon β, Interferon γ, erythropoietin (EPO), thrombopoietin (TPO), G-CSF, HGF, tissue plasminogen activator (tPA), stem cell factor, TGF family and their derivatives.

It is not necessary to continuously or periodically add methanol for the entire culturing period in the present invention. According to a preferable embodiment of the present invention, a medium contains 1 to 2% (v/v) methanol at the start of culturing after which culturing is performed for at least 12 hours, for example, 15 to 20 hours, without adding methanol. Continuous or periodic addition of methanol is then started when the methanol concentration decreases to about 0.5% (v/v) or less, and for example, 0.2 to 0.5% (v/v). At this point, since the microorganisms have grown quite extensively and there is active consumption of methanol, the methanol concentration in the medium will continue to decrease, eventually falling to substantially 0% to 0.1% if the methanol addition rate is suitable.

Addition of methanol is then continued under these conditions. During the time of methanol addition in this manner, the promoter is induced by methanol causing expression of the target gene. In parallel with this, the added methanol is used at least as a portion of growth materials resulting in growth of the microorganisms. Namely, according to the present invention, expression of a gene due to induction of a promoter by methanol, and particularly the production of a target useful protein, along with growth of the microorganisms are carried out simultaneously and in parallel over at least a certain period of time during the culturing period. Thus, in the method of the present invention, there is no need for the culturing period to be divided into a period during which a promoter is induced by methanol and a period for microorganism growth.

The microorganisms used in the method of the present invention are preferably methylotrophic yeasts, and preferably microorganisms belonging to the genus *Pichia, Hansenula* or *Candida*. Examples of yeasts belonging to these genuses include *Pichia pastoris, Hansenula polymorpha* and *Candida boidinii*.

Next, the following provides a more detailed explanation of the present invention. The present invention can be used to efficiently produce a target gene product in a gene expression system using a methanol-inducible promoter and microorganisms having a methanol metabolic pathway for the host. In the present invention, although *Candida boidinii* has been indicated as a specific example of a microorganism having a methanol metabolic pathway, a promoter of alcohol oxidase gene of *Candida boidinii* has been indicated as a specific example of a promoter, and secretory Kex2 derivative has been indicated as a specific example of a target gene product, these are not limited to the specific examples indicated.

A study of culturing conditions was conducted using *Candida boidinii* strain TK62 (pCU660) #10. Strain TK62 (pCU660) #10 is a secretory Kex2 derivative high producing-strain that was selected based on the production and secretion of Kex2 derivative in a test tube scale culture from 20 clones of strain TK62 containing secretory Kex2 derivative expression vector pCU660. The following provides an explanation of the production of Kex2 derivative expression vector pCU660 and strain TK62 of the host.

Plasmid pCU660 is a plasmid that is able to express secretory Kex2 derivative by AOD promoter, and was prepared by inserting a DNA fragment containing secretory Kex2 derivative gene into the Not I site of pNOTe1I (Japanese Unexamined Patent Publication No. 5-344895). The polypeptide from the N terminal to the 660th amino acid residue missing the membrane spanning domain present on the C terminal of the Kex2 protease (814 amino acid residues) of *Saccharomyces cerevisiae* (to be referred to as Kex2-660) was used for the secretory Kex2 derivative.

The DNA fragment containing the NKEX2-660 gene (−132 to 1980 nucleotides; taking A of the starting methionine codon of the KEX2 gene (structural gene of Kex2 protease) to be 1; Mizuno, et al., Biochem. Biophys. Res. Commun. 156, pp. 246–254, 1988) was prepared by amplifying with PCR using NKEX2 and KM088 for the primers and DNA coding for KEX2 gene for the template.

Primer NKEX2 is a DNA oligomer containing a DNA sequence corresponding to the 107 to 132 nucleotides upstream from the starting methionine codon of the KEX2 gene, and the sequence resulting from the addition of an NotI restriction enzyme recognition site to its 5' flanking region. KM088 is a DNA oligomer having a sequence complimentary to a nucleotide sequence resulting from the addition of translation stop codon TAA to DNA corresponding to 654th to 660th amino acids of Kex2 protease. In addition, pCU660 is chromosome-inserting expression vector having a URA3 gene as a selection marker (the unique BamHI restriction enzyme site is located in this gene). If a uracil-requiring strain obtained by URA mutation is used as a host, transformants can be selected according to the complementarity of the uracil requirement.

Strain TK62 is a uracil-requiring strain derived from *Candida boidinii* strain S2 AOU-1, obtained by URA3 mutation and has a group of enzymes for a methanol metabolic pathway, that includes alcohol oxidase, thereby enabling it to grow using methanol for its carbon source. In addition, the amount of alcohol oxidase expressed by strain TK62 is high at about 40% of the intracellular protein in culturing using methanol for the carbon source, and a heterogeneous gene expression system using this promoter has previously been disclosed (Japanese Unexamined Patent Publication No. 5-344895).

Next, a study of culturing conditions using the above-mentioned strain TK62 (pCU660) #10 was conducted. The methanol concentration in the culture medium is an extremely important parameter for the growth of microorganisms having a methanol metabolic pathway and for efficient induction of transcription from a methanol-inducible promoter. Therefore, strain TK62 (pCU660) #10 was cultured using a jar fermenter to study the conditions that affect host growth such as the conditions under which methanol is added to the culture medium.

First, culturing was performed using methanol and glycerol for the carbon sources. At the start of culturing, the cell density was set to a culture medium turbidity of OD600=0.2, while the initial carbon sources were set to a methanol concentration of 1.5% (v/v) in consideration of cell toxicity, and to a concentration of 3% (w/v) for glycerol in consideration of osmotic pressure. The methanol concentration of the culture medium was measured every 3 hours, and the times and amounts of methanol addition to the culture medium were determined with reference to the concentration 2 to 3 hours earlier. Methanol and glycerol were added periodically by operating a peristaltic pump having a constant delivery volume per unit time for a fixed amount of time once every 7.5 minutes.

Addition rate was represented by the amount methanol (ml/L.h) or glycerol (g/L.h) added per 1 liter of culture medium per hour. Since the methanol concentration of the culture medium at 15 hours after the start of culturing decreased to 0.42% (v/v), methanol addition was started at a rate of 0.75 ml/L.h 18 hours after the start of culturing. Furthermore, the methanol concentration of the culture medium had decreased to 0.26% (v/v) in 18 hours after the start of culturing immediately before the start of addition.

Since the methanol concentration of the culture medium at 21 hours after the start of culturing had decreased to 0.1% (v/v) or less, the methanol addition rate was increased to 7.5 ml/L.h starting 23 hours after the start of culturing. Immediately after this addition, the stirring rate decreased rapidly and a sudden decrease in the oxygen consumption rate of the yeast, namely a decrease in cellular activity, were observed. After these decreases, it was expected that cell density decreased and the yeast lysed. The methanol concentration of the culture medium at 1 hour, after the increase of the methanol addition rate (24 hours after the start of culturing), was 0.76% (v/v), and it was found that methanol was accumulating.

Based on the above results, it was found that 1) a good time for starting the addition of methanol to the culture medium is in the 18th hour after the start of culturing (OD600=approx. 50), 2) since the methanol concentration of the culture medium decreases to 0.1% (v/v) or less within 3 hours at a methanol addition rate of 0.75 ml/L.h, there is a possibility of a shortage of methanol for the carbon source, and 3) there is a possibility of cell toxicity occurring due to accumulation of methanol in the culture medium due to the addition rate of 7.5 ml/L.h being excessively high. In addition, in culturing yeast strain TK62 (pCU660) #10 having a methanol metabolic pathway, it was found that after a state continues in which the methanol concentration in the culture medium is 0.1% (v/v) or less, rapid addition of methanol causes strain TK62 (pCU660) #10 to be killed.

Moreover, the fluctuations in dissolved oxygen values synchronous to the methanol addition cycle (consisting of repetition of a sudden increase, maintenance of high values and a sudden decrease) were observed from the 20th to 23rd hours after the start of culturing. Since this period coincided with the time from when the methanol concentration of the culture medium decreased to 0.1% (v/v) or less to the time when methanol began to accumulate due to rapid addition of methanol to the culture medium (namely, the time during which the methanol concentration of the culture medium was 0.1% (v/v) or less), it was suggested that there is relationship between the periodic fluctuations in dissolved oxygen values and the methanol concentration in the culture medium.

The amount of dissolved oxygen is a parameter that is normally monitored for culture control, and is measured using a dissolved oxygen electrode. If it were possible to predict the required amount of methanol based on changes in the amount of dissolved oxygen in the culturing of microorganisms having a methanol metabolic pathway, it would be possible to easily set stable and efficient culture conditions. Therefore, in order to investigate in detail the relationship between fluctuations in dissolved oxygen values synchronized with the methanol addition cycle and the methanol concentration of the culture medium, culturing was performed by setting the methanol addition rate to 2.25 ml/L.h, intermediate to the rate of 0.75 ml/L.h at which methanol concentration in the culture medium decreased rapidly, and the rate of 7.5 ml/L.h at which methanol accumulated in the culture medium in the above-mentioned culturing.

Methanol was added with glycerol (0.15 ml/L.h) starting at the 18th hour after the start of culturing. Fluctuations in dissolved oxygen values, synchronized with the addition cycle of the carbon sources were observed from the 23rd hour after the start of culturing to the completion of culturing (49 hours after the start of culturing).

The methanol concentration in the culture medium during this time was 0.1% (v/v) or less. Namely, during the time fluctuations in dissolved oxygen values that are synchronous with the methanol addition cycle are observed, methanol did not accumulate in the culture medium, and the concentration could be confirmed to be 0.1% (v/v) or less. In addition, it was also clear that during the time the methanol concentration was 0.1% (v/v) or less (23–49 hours after the start of culturing), the number of cells increased more than two times. In other words, cells were able to grow even though the methanol concentration of the culture medium was 0.1% (v/v) or less.

Moreover, when the methanol concentration of the culture medium was 0.1% (v/v) or less and the glycerol concentration was also 0.1% (w/v) or less, the amount of change in the periodic fluctuations in dissolved oxygen values synchronous with the addition cycle of the carbon source solution increased. When glycerol was added so that the final concentration in the culture medium at this time became 1.25% (w/v), although the increased amount of change returned to normal, the periodic fluctuations in dissolved oxygen values synchronous with the addition cycle of the carbon source solution themselves continued.

Namely, it was clear that periodic fluctuations of dissolved oxygen values indicate that the methanol concentration of the culture medium is 0.1% (v/v) or less, and an increase in that amount of change indicates a state in which the methanol concentration in the culture medium is 0.1% (v/v) or less and that the glycerol concentration is 0.1% (w/v) or less. By using these indicators, the state in which the methanol concentration is 0.1% (v/v) or less and the glycerol concentration is 0.1% (w/v) or less can be monitored, thereby enabling a suitable amount of addition to replenish these carbon sources to be determined.

The inventors of the present invention clarified the fact that, in the culturing of methylotrophic yeast that have a methanol metabolic pathway, the methanol addition rate that allows the yeast to grow without dying can be monitored with the periodic addition of methanol and the fluctuations in dissolved oxygen values in synchronization with that addition. Moreover, it was also clearly shown that during the time in which periodic fluctuations in dissolved oxygen values are observed synchronously with periodic methanol addition, the culture is in a state in which the methanol concentration is 0.1% (v/v) or less and there is no accumulation of methanol in the culture medium, namely the state in which the amount of methanol added is equal to the amount of methanol consumed by the yeast. Therefore, an attempt was made to measure the rate of methanol consumption in a state of high cell density using as an indicator the periodic fluctuations in dissolved oxygen values synchronous with the addition of methanol.

Similarly, during culturing of strain TK62 (pCU660) #10 to a cell density of 65 g DCW/L (OD600=270), methanol was added at addition rates of 1.5, 2.2, 4.7 and 6.4 ml/L.h (equivalent to additions of 0.023 to 0.098 ml per hour per 1 g of yeast dry weight (ml/g DCW.h)), and the periodic fluctuation patterns of dissolved oxygen values and methanol concentrations in the culture medium at those times were examined. As a result, it was found that dissolved oxygen values fluctuated synchronously with methanol addition when the methanol addition rate was 1.5 to 4.7 ml/L.h, and that the methanol concentrations in the culture medium at those times were all 0.1% (v/v) or less.

Moreover, the fluctuation pattern changed with increases in the methanol addition rate, and it was found that the increase in dissolved oxygen values per unit time following addition of methanol became more gradual. When the methanol addition rate became 6.4 ml/L.h, periodic fluctuations in dissolved oxygen values synchronous with the methanol addition cycle were no longer observed. Although the methanol concentration in the culture medium at this time was 0.1% (v/v) or less, when the methanol addition rate was further increased, the methanol in the culture medium was found to accumulate.

As has been described above, the inventors of the present confirmed that, in a culture in which the methanol addition rate is changed, at least when dissolved oxygen values fluctuate synchronously with the periodic addition of methanol, methanol added to the culture medium is immediately consumed and does not accumulate in the culture medium. In other words, a state is reached in which the amount of methanol added is equal to the amount of methanol consumed by the yeast. Moreover, it was also clearly shown that the periodic fluctuation pattern of dissolved oxygen values changes according to the amount of methanol added, or in other words, according to the time until the methanol is completely consumed, and the maximum amount of methanol consumed by the yeast at each time (amount of methanol added immediately before accumulation) can be monitored without taking samples.

The maximum rate of methanol consumed in the state in which cell density is 65 g DCW/L (OD600=270) was determined to be 0.098 ml/g DCW.h based on these findings.

The maximum rate of methanol consumed when the cell density of strain TK62 (pCU660) #10 is OD600=270 (65 g of dry cell weight/L of culture medium) is 0.098 ml/g DCW.h, and in the case the methanol addition rate is equal to or less than this value, methanol does not accumulate in the culture medium. However, although it can be easily predicted that the methanol addition rate suitable for growth of strain TK62 (pCU660) #10 and for secretory production of Kex2-660 is equal to or less than the maximum methanol consumption rate, it was unknown as to which addition rate is the most suitable.

In order to investigate the suitable methanol addition rate for growth of strain TK62 (pCU660) #10 and for secretory production of Kex2-660, culturing was performed using a methanol addition rate of 2.25 ml/L.h or 4.5 ml/L.h, and cell growth rate and secretory production of Kex2-660 at those times were examined. As a result, it was clearly shown that cells increase and Kex2-660 is expressed and secreted into the culture medium during the time the methanol concentration in the culture medium at which fluctuations in dissolved oxygen values are observed synchronous with the methanol addition cycle is 0.1% (v/v) or less.

Namely, the methanol addition rate at which the methanol concentration in the culture medium is 0.1% (v/v) or less and dissolved oxygen values fluctuate synchronous with periodic methanol addition was found to be the suitable rate for cell growth and expression of the target product. Moreover, as a result of comparing cultures using methanol addition rates of 2.25 ml/L.h and 4.5 ml/L.h, the number of cells at 48 hours after the start of culturing increased by 1,400 times and 1,800 times, respectively, from the start of culturing, while the amount of Kex2-660 produced and secreted was 1260 MU and 2850 MU, respectively, per liter of culture supernatant (equivalent to approximately 150 mg and 340 mg, respectively) (Table 1). It was clearly shown that as long as methanol addition conditions are maintained such that periodic fluctuations in dissolved oxygen values continue, cell growth increases and production of Kex2-660 increases with increasing amounts of methanol added.

Moreover, in the culturing of strain TK62 (pCU660) #10 during which methanol was added at the rates of 2.25 ml/L.h and 4.5 ml/L.h starting on the 18th hour after the start of culturing, it was clear that the rate of methanol consumption when the dry yeast weight is 0.5 g/L (OD600=2) or higher is 0.03 to 0.16 ml/g DCW.h (Table 2).

TABLE 1

| Addition rate (ml/L · h) | OD$_{600}$ | Kex2 activity (kU/ml of supernatant) |
|---|---|---|
| 2.25 | 284 | 1260 |
| 4.5 | 353 | 2850 |

* Glycerol addition rate is 5 g/l · h.
OD600 Kex2 activity was measured in the 48th hour after the start of culturing.

TABLE 2

| MeOH addition rate (ml/L · h) Culturing time (h) | DCW (g/L) | | MeOH consumption rate (ml/g DCW · h) | |
|---|---|---|---|---|
| | 2.25 | 4.5 | 2.25 | 4.5 |
| 6  | 0.2  | 0.5 | 4.24 | 1.77 |
| 12 | 2.4  | 3.3 | 0.10 | 0.05 |
| 18 | 12.  | 13  | 0.11 | 0.09 |
| 24 | 28   | 31  | 0.09 | 0.16 |
| 30 | 43   | 48  | 0.05 | 0.09 |
| 36 | 44   | 59  | 0.05 | 0.08 |
| 42 | 60   | 71  | 0.04 | 0.06 |
| 48 | 68   | 85  | 0.03 | 0.05 |

DCW: Yeast dry cell weight per liter of culture medium.
MeOH consumption rate: Mean value of 0 to 6 hours in the case of a culturing time of 6 hours, and applied similarly for other culturing times.

In addition, the 48 hours of culturing time to product the above-mentioned Kex2 is short at only ⅓ to ½ the 100 to 160 hours required to obtain the target gene product by dividing into the methylotrophic yeast growth phase (approx. 40 hours) and production phase (60 to 120 hours) indicated in WO 95/21928, thereby clearly indicating the usefulness of the present invention in the case of substance production at the industrial level.

Furthermore, Examples in which periodic fluctuations in dissolved oxygen values produced by periodic addition of methanol are evaluated by computer to automatically control culturing are not shown. However, in culturing using a jar fermenter, the amount of dissolved oxygen, pH and temperature are basic parameters for controlling culturing, and their values are measured over time using a DO sensor, pH sensor and temperature sensor, respectively, to evaluate these values by computer and automatically control culturing.

When controlling these parameters, culturing is controlled not only with the values of each parameter but also with the amount of change of each parameter per unit time. Namely, a person with ordinary skill in the art can automatically control the amount of methanol added by determining the suitable amount of methanol to be added based on findings relating to periodic fluctuations in dissolved oxygen values synchronous with the periodic addition of methanol and the finding that the fluctuation pattern changes according to the rate of methanol addition as clarified by the inventors of the present invention.

EXAMPLES

Although the following provides a detailed explanation of the present invention using *Candida boidinii* as an example of a microorganism having a methanol metabolic pathway, the present invention is not limited to this example. In addition, although the promoter of alcohol oxidase is used as an example of a promoter for which expression is induced by methanol, and Kex2-660 is used as an example of a gene product to be produced in the detailed explanation, the present invention is not limited to these examples.

Example 1. Preparation of NKEX2-660 Gene and Expression Vector pCU660

A gene (NKEX2-660 gene) coding for secretory Kex2 derivative Kex2-660 (protein consisting of the amino acids from the N terminal to the 660th amino acid of Kex2 endoprotease), and NKEX2-660 expression vector pCU660 were prepared in the manner described below.

1) Preparation of NKEX2-660 Gene (see FIG. 1)

A DNA fragment containing the NKEX2-660 gene was prepared by PCR using plasmid pYE-KEX2(5.0)b, cleaved with restriction enzyme Eco RI and formed into a straight chain (Mizuno et al., Biochem. Biophys. Res. Commun. 156, 246–254, 1988), for the template and using NKEX2 (SEQ ID NO.: 1) and KM088 (SEQ ID NO.: 2) for the primers.

Figure 1A:
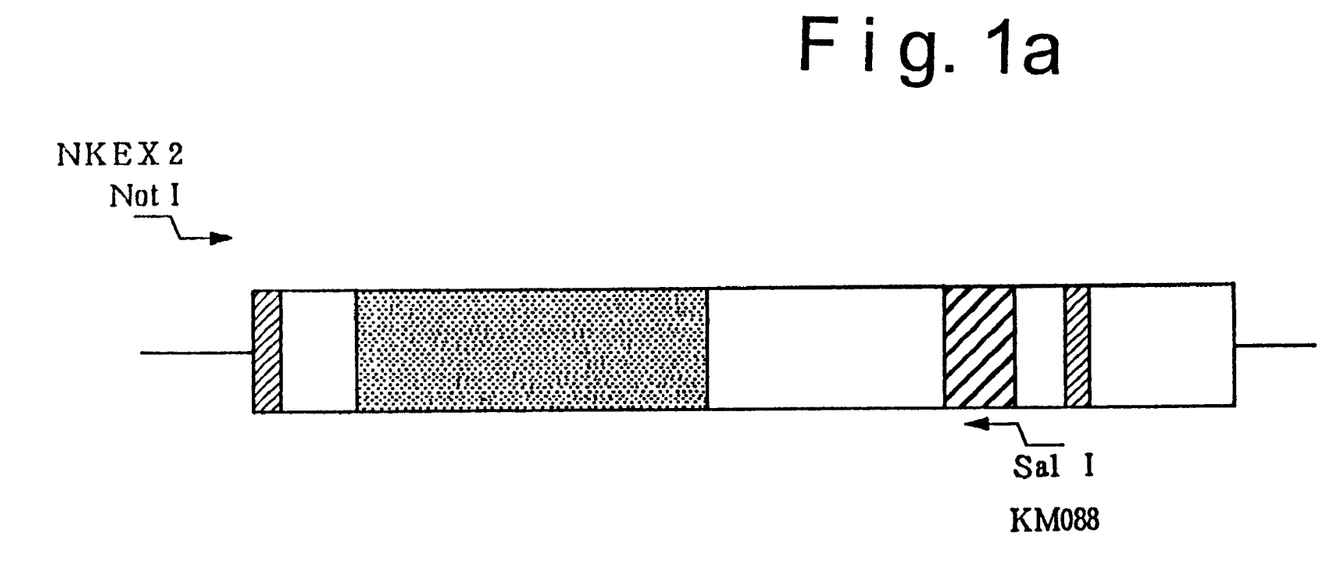
FIG. 1 is an illustration schematically indicating the structure of the Kex2 protease gene, the sequences of the primers used for synthesis of NKEX2-660 gene, and the gene regions at which the primers are annealed.
Figure 1B:
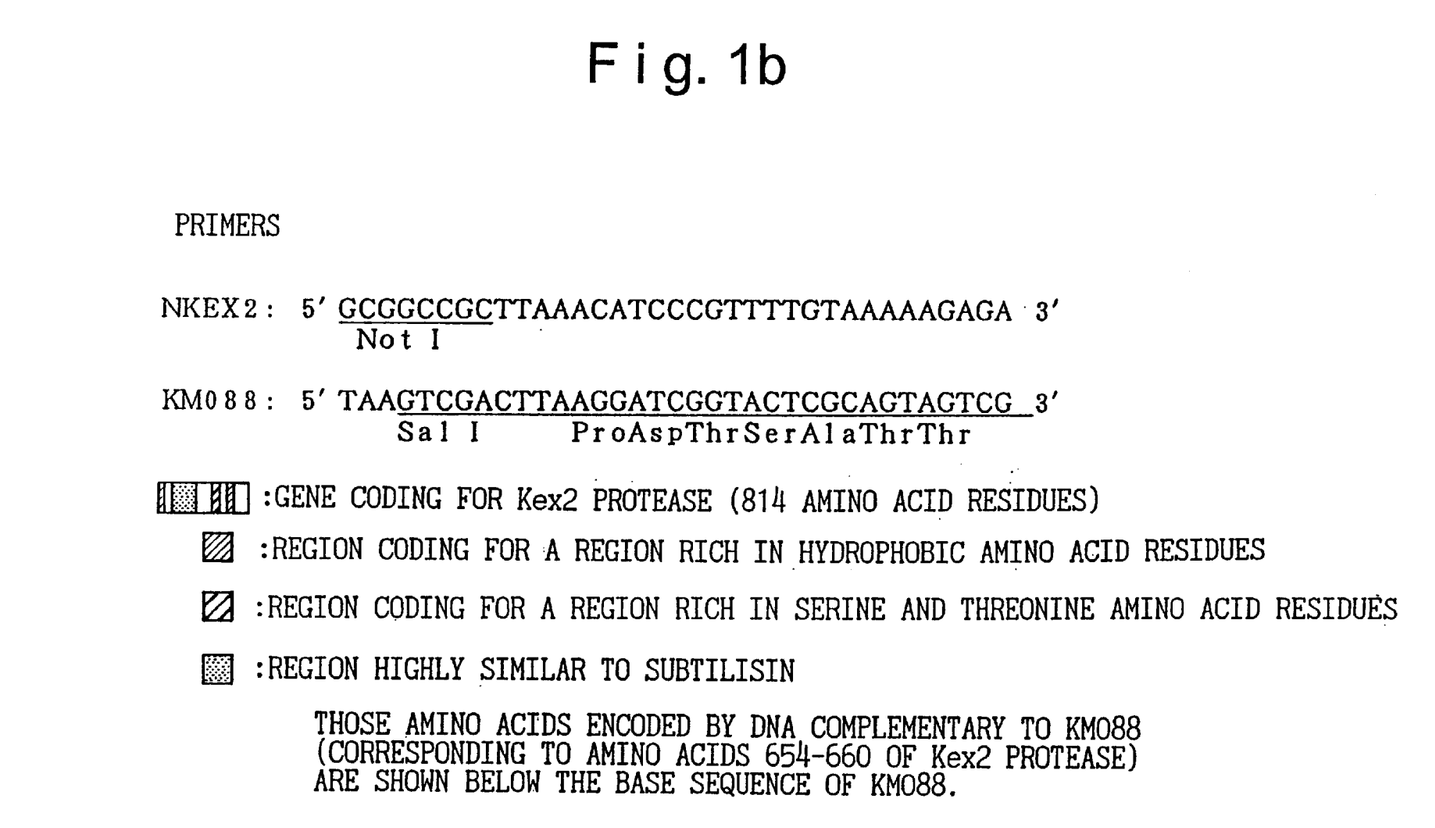

NKEX2 and KM088 correspond to the KEX2 gene regions shown in FIG. 1(a), NKEX2 contains a sequence corresponding to 107 to 132 nucleotides upstream from the starting methionine codon of the KEX2 gene, and KM088 has a nucleotide sequence complementary to the nucleotide sequence resulting from addition of a translation stop codon TAA to DNA corresponding to the amino acids from amino acid 654 to amino acid 660 of Kex2 protease (Mizuno, et al., Biochem. Biophys. Res. Commun. 156, p. 246–254, 1988). In addition, NKEX2 has the nucleotide sequence of the restrictase Not I site on its 5' terminal (underlined), while KM088 has the nucleotide sequence of the restriction enzyme Sal I site (underlined) (see FIG. 1(b)). These primers were synthesized with an automatic synthesizer (Applied Biosystems Model 380A) according to the phosphoamidide method.

Figure 2:
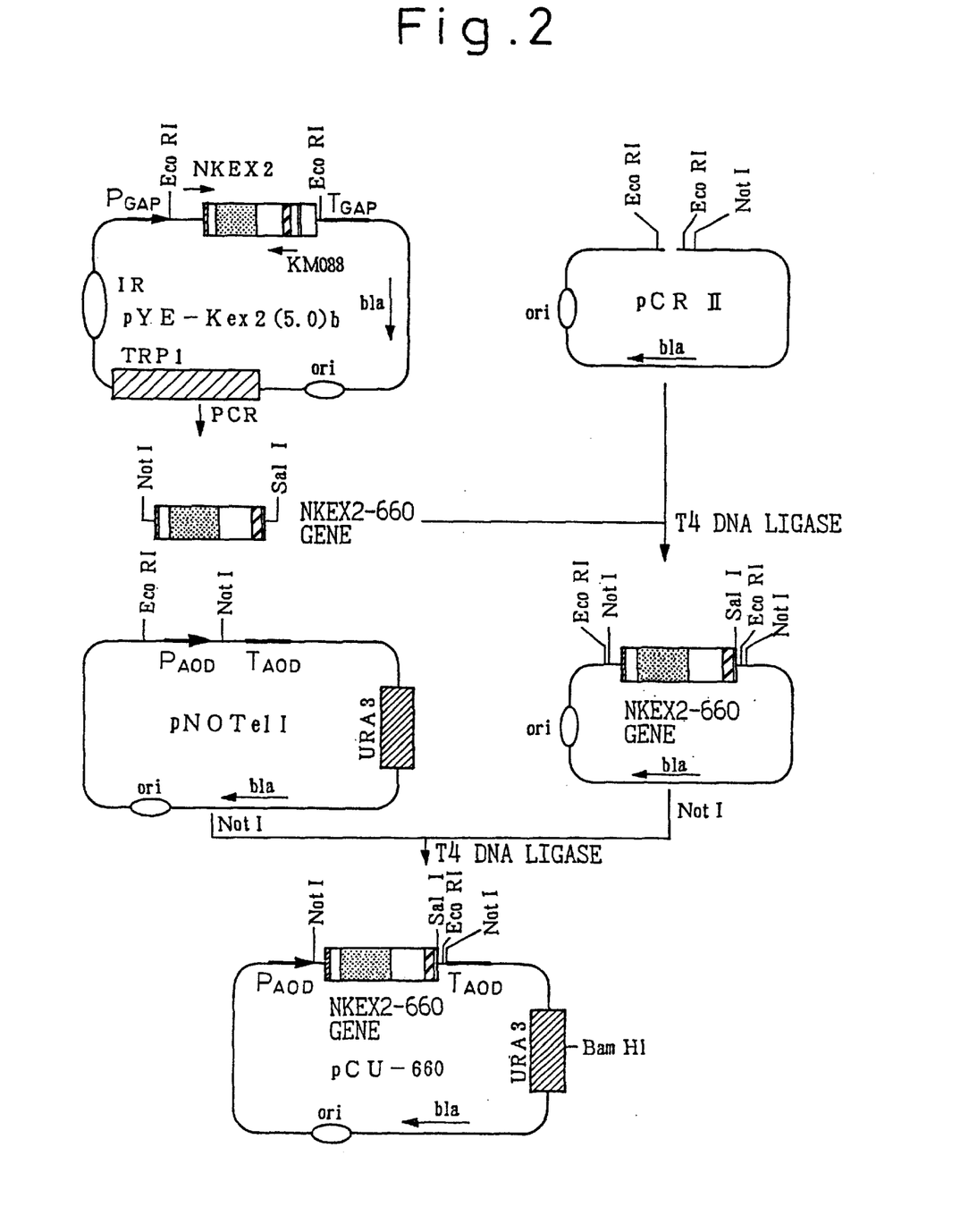
FIG. 2 is an illustration indicating a process for construction of pCU660.

2) Preparation of Expression Vector pCU660 (see FIG. 2)

Expression vector pCU660 was prepared by inserting a Not I DNA fragment containing NKEX2-660 gene into the Not I restriction enzyme site of expression plasmid pNOTe1I (Japanese Unexamined Patent Publication No. 5-344895) using *Candida boidinii* for the host so that KEX2-660 gene can be expressed under the control of alcohol oxidase gene (AOD) promoter (FIG. 2).

For the vector, pNOTe1I was cleaved with restriction enzyme Not I and the about 7.4 kb DNA fragment was purified. The Not I DNA fragment containing NKEX2-660 gene was prepared by cloning a DNA fragment containing the NKEX2-660 gene of 1) to pCRII (Invitrogen), and then cleaving using the restriction enzyme Not I sites present on NKEX2 and pCRII. Furthermore, pNOTe1is a vector that enables the target gene to be expressed by AOD promoter, and has a URA3 gene for the selection marker in the case of using yeast as a host, and ampicillin resistance in the case of using *E. coli* as a host. Consequently, if a yeast is used as a host that requires uracil, transformant strains can be selected on a plate that does not contain uracil.

Example 2. Isolation of Transformant and Kex2-Producing Strain

Plasmid pCU660 cleaved with restriction enzyme Bam HI and formed into a straight chain was introduced into uracil-requiring strain TK62, and chromosome-inserting recombinant strain TK62 (pCU660) was selected by using the complementarity of the uracil requirement. Strain TK62 is a uracil-requiring strain produced by URA3 mutation that is derived from *Candida boidinii* strain S2 AOU-1, and the transformation method of strain TK62 has been reported by Sakai, et al. (Sakai, Y. et al., J. Bacteriol., 173, 7458–7463, 1991). Strain S2 AOU-1 has been named *Candida boidinii* SAM1958, and was deposited in Institute of Bioengineering and Human Technology Agency of Industrial Science and Technology on February 25, 1992 as FERM BP-3766).

pCU660 is a chromosome-inserting expression vector, and for the resulting transformant TK62 (pCU660) the amount of Kex2 derivative expressed and the amount secreted may be different according to the chromosome insertion site of the gene, the number of copies and so forth. Twenty transformant clones (#1 through #20) were cultured at the test tube level and the amount of Kex2 derivative secreted into the culture medium (Kex2 protease activity) was investigated to select clones secreting large amounts of Kex2 derivative.

First, 20 strains of TK62 (pCU660) #1 through #20 were shake-cultured at 27° C. in BMGY medium (1% (w/v) yeast extract, 2% (w/v) peptone, 1% (w/v) glycerol, 1.34% (w/v) YNB wo AA: Yeast Nitrogen Base without Amino Acids, 0.4 mg/L biotin and 100 mm potassium phosphate (pH 6.0)). TWO days later, the culture medium was inoculated into 1 ml of BMMY medium (1% (w/v) yeast extract, 2% (w/v) peptone, 0.5% (w/v) methanol, 1.34% (w/v) YNB wo AA, 0.4 mg/L biotin and 100 mM potassium phosphate (pH 6.0)) so that OD600 was 10, followed by shake culturing at 27° C. Thirty hours later, the Kex2 activity of the supernatant was measured and five strains having the highest activity were selected. These five strains were cultured in a similar manner after which TK62 (pCU660) strain #10 was selected and used in the following experiment due to its consistently high levels of Kex2 activity.

Measurement of Kex2 activity was performed in compliance with the method of Mizuno, et al. (Mizuno et al., Biochem. Biophys. Res. Commun., 156, 246–254, 1988). Namely, 100 μl of Kex2-600 diluted with 100 mM Tris-HCl (pH 7.0) were added to 100 μl of 200 mM Tris-HCl (pH 7.0) solution containing 2 mM $CaCl_2$, 0.2% (w/v) luburol and 100 μM Boc-Leu-Arg-Arg-MCA (Peptide Research), and allowed to stand for 30 minutes at 37° C. After adding 50 μl of 25 mM EGTA, the fluorescence intensity of the cleaved AMC was measured using the PANDEX FCA system (Baxter-Travenol: Model 10-015-1, excitation=365 nm, emission =450 nm). The amount of Kex2 activity that releases 1 pmol of AMC in 1 minute under the above-mentioned conditions was defined as 1 U of activity.

Example 3. Setting of Culturing Conditions (see FIG. 3)

1) Basic Culturing Conditions

Preculture was performed by inoculating 1 ml of strain TK62 (pCU660) #10 from glycerol frozen stock into a 300 ml Erlenmeyer flask containing 25 ml of YPD medium (1% (w/v) yeast extract, 2% (w/v) peptone, 2% (w/v) glucose) and shake culturing for 16 hours at 27° C.

Main culturing was performed by inoculating the above-mentioned precultures into 2 liters of culture medium (1.5% (v/v) methanol, 3% (w/v) glycerol, 1% (w/v) yeast extract, 2% (w/v) peptone, 50 mM potassium phosphate (pH 6.0) and 1.34% (w/v) YNB wo AA) so that the cell density at the start of culturing was OD600=0.2, and stirring while aerating at 27° C. using a 5 liter volume fermenter (Mitsuwa Scientific Instruments, Model KMJ-5B-4U-FP). The aeration rate was set at 4 L/min, and the stirring rate was controlled so that the amount of dissolved oxygen did not fall below 2.5 ppm. The nitrogen of the culture was suitably replenished with 80 ml of nitrogen source replenishing solution (5% (w/v) yeast extract, 10% (w/v) peptone, 6.7% (w/v) YNB wo AA), and the pH was controlled so as not to fall below 5.5, by the addition of 7.5% ammonia water.

0.5 ml/L of antifoaming agent (Disfoam CC-222, Nippon Yushi) was added at the start of culturing, and added after that time as necessary. Replenishment of the carbon source was performed using a 15 to 45% (v/v) methanol solution and a 10 to 50% (w/v) glycerol solution (concentrations were changed according to culturing). Methanol and glycerol were added periodically by operating a peristaltic pump having a constant delivery volume per unit time for a fixed amount of time once every 7.5 minutes. The addition rate was represented with the amount of methanol (ml/L.h) or amount of glycerol (g/L.h) added per liter of culture medium per hour.

2) Study of Methanol Addition Conditions

The concentration of methanol in the culture medium is an important parameter for growth of methylotrophic yeast strain TK62 (pCU660) #10, having a methanol metabolic pathway, and for expression of Kex2-660 from an AOD promoter for which expression is induced by methanol. The inventors of the present invention first attempted to set the conditions for addition of methanol in order to maintain the methanol concentration in the culture medium at a concentration that is sufficient as a carbon source for yeast growth as well as that which does not exhibit cell toxicity. Culturing was performed in accordance with basic culturing conditions.

The methanol concentration of the culture medium was measured every 3 hours, and the times and amounts of methanol addition to the culture medium were determined with reference to concentrations 2 to 3 hours earlier. Since the methanol concentration in the culture medium had decreased to 0.42% (v/v) 15 hours after the start of culturing (OD600=22), addition of methanol was started at a rate of 0.75 ml/L.h starting 18 hours after the start of culturing (OD600=52). Furthermore, the methanol concentration in the culture medium in the 18th hour after the start of culturing immediately before addition of methanol had decreased to 0.26% (v/v).

Since the methanol concentration in the culture medium in the 21st hour after the start of culturing had further decreased to 0.1% (v/v) or less, the rate of methanol addition was increased to 7.5 ml/L.h starting at the 23rd hour after the start of culturing (10 times faster than the initial addition rate). Immediately after this increase in the addition rate, the stirring rate rapidly decreased and the rate of oxygen consumption by the yeast decreased suddenly. Namely, a decrease in cell activity was observed. Later, cell density decreased and the yeasts were thought to have lysed. The methanol concentration of the culture medium at 1 hour after the methanol addition rate was increased (24 hours after the start of culturing) was 0.76% (v/v), thus indicating that methanol was accumulating in the culture medium.

On the basis of the above results, it was found that 1) a good time for starting addition of methanol to the culture medium is in the 18th hour after the start of culturing (OD600 =approx. 50), 2) since the methanol concentration of the culture medium decreases to 0.1% (v/v) or less within 3 hours at a methanol addition rate of 0.75 ml/L.h, there is a possibility of a shortage of methanol for the carbon source, and 3) there is the possibility of cell toxicity occurring due to accumulation of methanol in the culture medium due to the addition rate of 7.5 ml/L.h being excessively fast. In addition, it was found that after a state continues in which the methanol concentration in the culture medium is 0.1% (v/v) or less, rapid addition of methanol causes strain TK62 (pCU660) #10 to be killed.

Fluctuations in dissolved oxygen values synchronous with the cycle of methanol addition were observed from the 20th to 23rd hours after the start of culturing. Since this period coincided with the time from when the methanol concentration of the culture medium decreased to 0.1% (v/v) or less to the time when methanol began to accumulate due to rapid addition of methanol to the culture medium (namely, the time during which the methanol concentration of the culture medium was 0.1% (v/v) or less), it was suggested that there is the relationship between the periodic fluctuations in dissolved oxygen values and the methanol concentration in the culture medium.

3) Fluctuations of Dissolved Oxygen Values and Methanol Concentration in the Culture Medium In the culture to which methanol was periodically added in the previous section, it was suggested that fluctuations in dissolved oxygen values synchronous with the cycle of that addition are observed when the methanol concentration in the culture medium was 0.1% (v/v) or less, and are no longer observed when methanol begins to accumulate in the culture medium. The amount of dissolved oxygen is a routinely monitored parameter for culture control, and is measured using a dissolved oxygen electrode. If it were possible to predict the required amount of methanol based on changes in the amount of dissolved oxygen in the culturing of microorganisms having a methanol metabolic pathway, it would be possible to easily set stable and efficient culture conditions.

Therefore, a detailed investigation was conducted regarding the relationship between fluctuations in dissolved oxygen values in synchronization with the methanol addition cycle and the methanol concentration of the culture medium by culturing using a methanol addition rate of 2.25 ml/L.h, which is intermediate to the rate of 0.75 ml/L.h, at which the methanol concentration in the culture medium decreased rapidly, and the rate of 7.5 ml/L.h at which methanol accumulated in the culture medium in the above-mentioned culturing of section 2).

Based on the results of section 2), the time at which methanol addition is started was set to the time at which OD600 reaches about 50 (roughly 18 hours after the start of culturing), and the addition rates of the carbon sources were set to 2.25 ml/L.h for methanol and 0.15 g/L.h for glycerol. Fluctuations in dissolved oxygen values synchronous with the cycle of carbon source addition began to be observed starting in the 23rd hour after the start of culturing (OD600= 97), and continued until completion of culturing (49 hours after the start of culturing; OD600=198).

Figure 3:
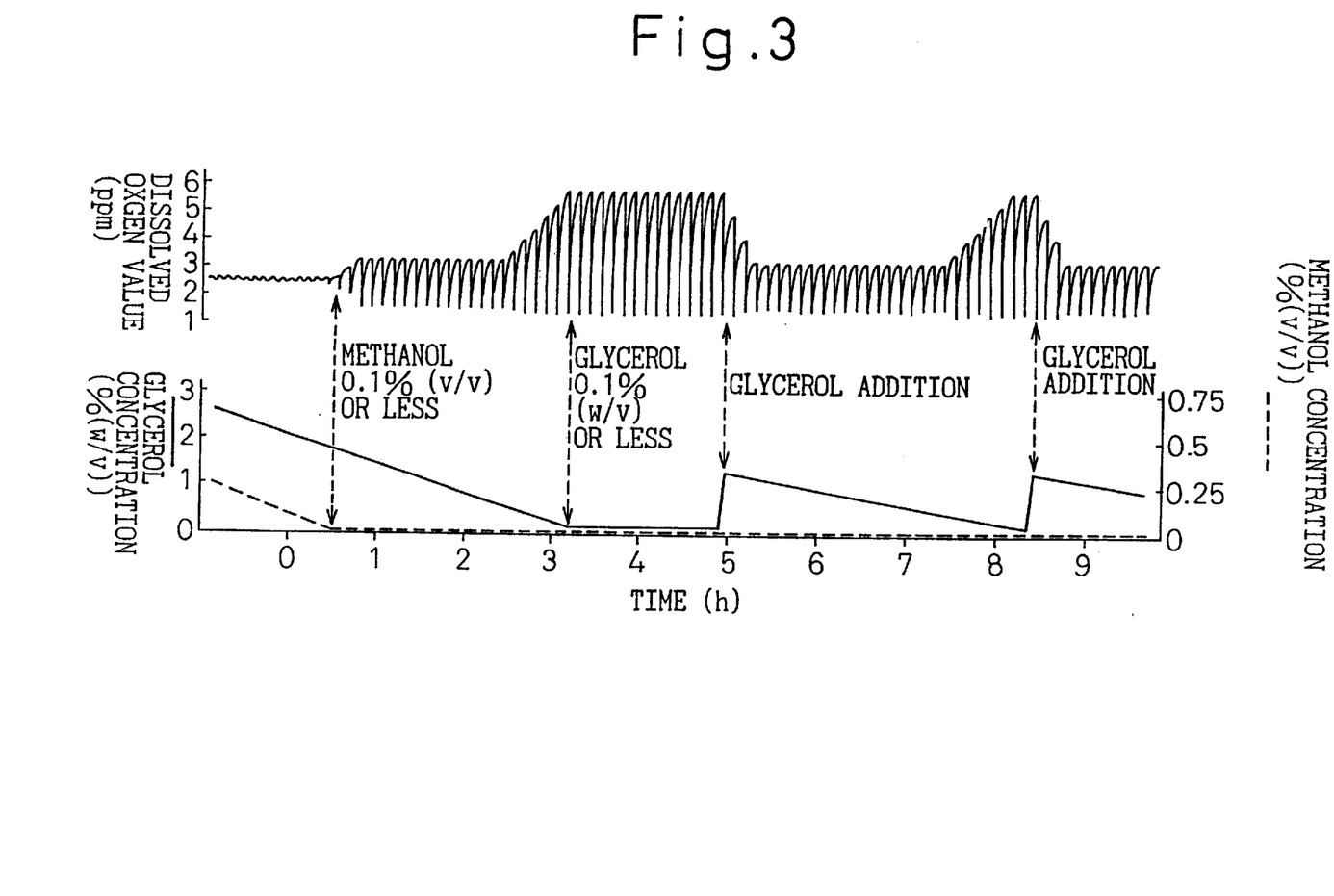
FIG. 3 is a graph indicating the fluctuations in dissolved oxygen values synchronous with the periodic addition of methanol observed when the methanol concentration in the culture medium is 0.1% (v/v) or less and the periodical change in the fluctuation pattern of dissolved oxygen when the glycerol concentration is 0.1% (w/v) or lower. The upper graph shows the fluctuations in dissolved oxygen values in the culture medium. The lower graph indicates the glycerol concentration in the culture medium with a solid line, and the methanol concentration with a broken line. The time when the methanol and glycerol concentrations have decreased to 0.1% (v/v) or less, and the time when glycerol is added are shown in the graph.

The methanol concentration in the culture medium during this time was 0.1% (v/v) or less. In addition, when the methanol concentration in the culture medium became 0.1% (v/v) or less and the glycerol concentration also became 0.1% (w/v) or less, the amount of change in the periodic fluctuations in dissolved oxygen values synchronous with the addition cycle of the carbon source addition solution increased (FIG. 3). When glycerol was added so that the final concentration in the culture medium at this time increased to 1.25% (w/v), although the increased amount of change returned to normal, it was found that the periodic fluctuations in dissolved oxygen values synchronous with the addition cycle of the carbon source addition solution themselves continued (FIG. 3).

Namely, it was clear that periodic fluctuations of dissolved oxygen values indicate that the methanol concentration of the culture medium is 0.1% (v/v) or less, and an increase in that amount of change indicates a state in which the methanol concentration in the culture medium is 0.1% (v/v) or less and that the glycerol concentration is 0.1% (w/v) or less. By using these indicators, the state in which the methanol concentration is 0.1% (v/v) or less and the glycerol concentration is 0.1% (w/v) or less can be monitored.

In addition, it was also clear that during the time the methanol concentration was 0.1% (v/v) or less (23–49 hours after the start of culturing), the number of cells increases more than two times doubled. In other words, cells were able to grow even though the methanol concentration of the culture medium was 0.1% (v/v) or less.

Example 4. Optimization of Methanol Addition Rate Based on the Periodic Fluctuation Pattern of Dissolved Oxygen Values The inventors of the present invention clearly demonstrated that during the time at which the methanol concentration in the culture medium in Example 3 is 0.1% (v/v) or less and the time at which the methanol does not accumulate in the culture medium, fluctuations in dissolved oxygen values are observed that are synchronous with the periodic addition of methanol, and that the fluctuations in dissolved oxygen values are no longer observed when methanol begins to accumulate. Moreover, it was also clearly shown that cells grow in the state in which fluctuations in dissolved oxygen values synchronous with the addition of methanol are observed. Therefore, a study was conducted to determine the relationship between methanol addition rate and the periodic fluctuations in dissolved oxygen values, and to clarify the relationship between the methanol addition rate and the amount of Kex2-660 secreted product.

1) Correlation Between Methanol Addition Rate and Periodic Fluctuations in Dissolved Oxygen Values The changes in the fluctuation patterns of dissolved oxygen values synchronous with periodic methanol addition when the methanol addition rate was changed were studied to determine whether the changes can serve as an indicator for controlling the addition of methanol to a culture medium.

When cell density reached OD600=270 (65 g DCW/L of culture medium) after the start of culturing, the methanol addition rate was changed to 1.5, 2.2, 4.7 and 6.4 ml/L.h, and the periodic fluctuation patterns of dissolved oxygen values and methanol concentrations in the culture medium at those times were examined. Glycerol was added simultaneously at the rate of 5 g/L.h. It was found that fluctuations in dissolved oxygen values in synchronization with methanol addition are observed when the methanol addition rate was 1.5, 2.2 or 4.7 ml/L.h, that the methanol concentrations in the culture medium at those times were all 0.1% (v/v) or less, and that the methanol does not accumulate. Moreover, it was found that the fluctuation pattern changed with increases in the methanol addition rate, and that the rate of increase in dissolved oxygen values per unit time following addition of methanol became more gradual (FIG. 4).

Figure 4:
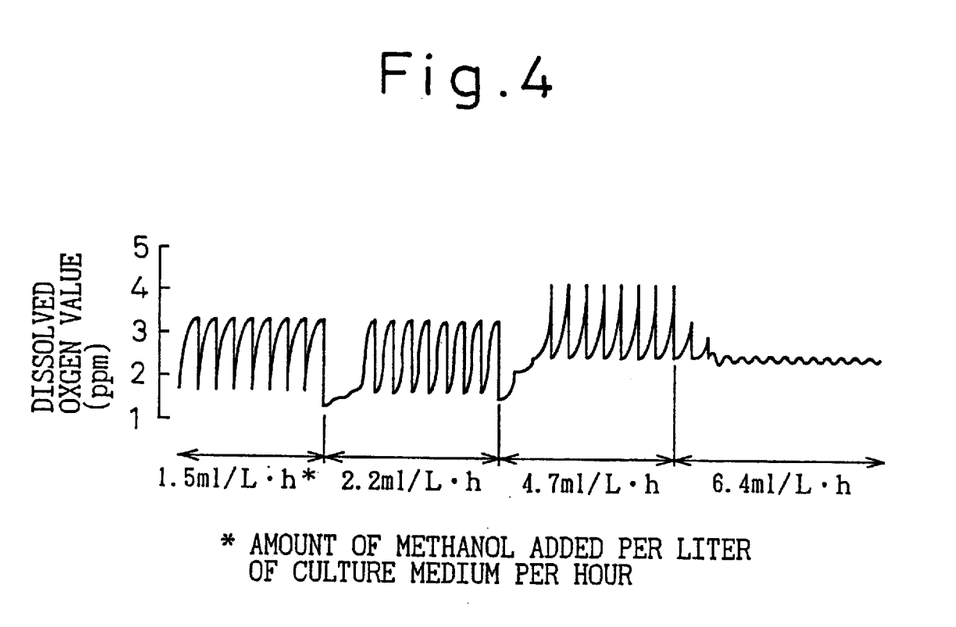
FIG. 4 is a graph illustrating the relationship between methanol addition rate and periodic fluctuations in dissolved oxygen values. The methanol addition rate is defined as the amount of methanol added per liter of culture medium per hour, and is indicated with the addition times (shown with arrows).

Moreover, when the methanol addition rate became 6.4 ml/L.h, periodic fluctuations in dissolved oxygen values synchronous with the methanol addition cycle were no longer observed (FIG. 4). Although the methanol concentration in the culture medium at this time was 0.1% (v/v) or less, when the methanol addition rate was further increased, the methanol in the culture medium was found to accumulate. Although the ability of yeast to consume methanol cannot be determined only by measuring the methanol concentration in the culture medium, based on the above results and those of section 2) of Example 3, it was determined that yeast have considerable margin for consuming methanol if the increase in dissolved oxygen values per unit time is rapid, and little margin for methanol consumption if the increase is gradual.

In other words, the need for adjustment of the rate of methanol addition can be determined by observing the periodic fluctuation pattern of dissolved oxygen values. Moreover, it has been clearly shown that in the state in which cell density is OD600=270, as long as the methanol addition rate does not exceed 4.7 ml/L.h, periodic fluctuations in dissolved oxygen values are observed, methanol does not accumulate, and strain TK62 (pCU660) #10 grows without being killed.

2) Methanol Addition Rate and Amount of Secreted Kex2-660 Produced

When the cell density of strain TK62 (pCU660) #10 is OD600=270 (65 g DCW/L culture medium), the methanol addition rate at which methanol does not accumulate in the culture medium and the yeast are not killed was within the range of 1.5 to 4.7 ml/L.h. Therefore, in order to investigate which of these methanol addition rates at which methanol does not accumulate in the culture medium is optimal for the growth rate of strain TK62 (pCU660) #10 and for the amount of secreted Kex2-660 produced, culturing was performed using a methanol addition rate of 2.25 ml/L.h or 4.5 ml/L.h, and the cell growth rates and secreted Kex2-660 production amounts at those times were determined. The glycerol addition rate was 5 g/L.h in both cases.

During culturing using a methanol addition rates of 2.25 and 4.5 ml/L.h, dissolved oxygen values began to fluctuate synchronously with the periodic addition of methanol starting 22 and 25 hours after the start of culturing, respectively, and the fluctuations continued until the 48th hour when culturing was completed. The methanol concentrations in the culture medium during this time were both 0.1% (v/v) or less.

Figure 5:
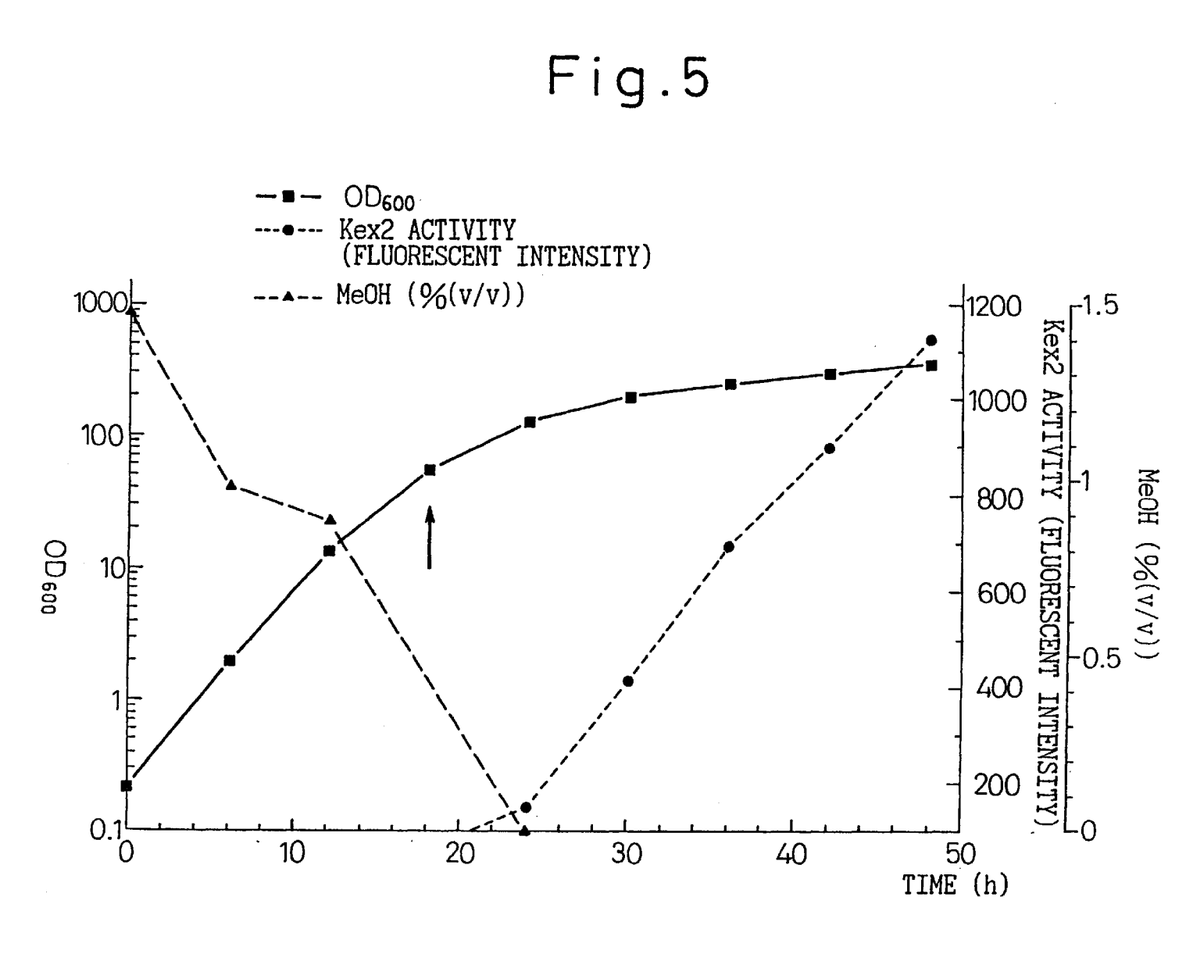
FIG. 5 is a graph illustrating an example of the production of Kex2-660 in culturing using a methanol addition rate of 4.5 ml/l.h. OD600 values are indicated with solid squares, Kex2 activity (fluorescent intensity) with solid circles, and methanol concentration in the culture medium with solid triangles.
Figure 6:
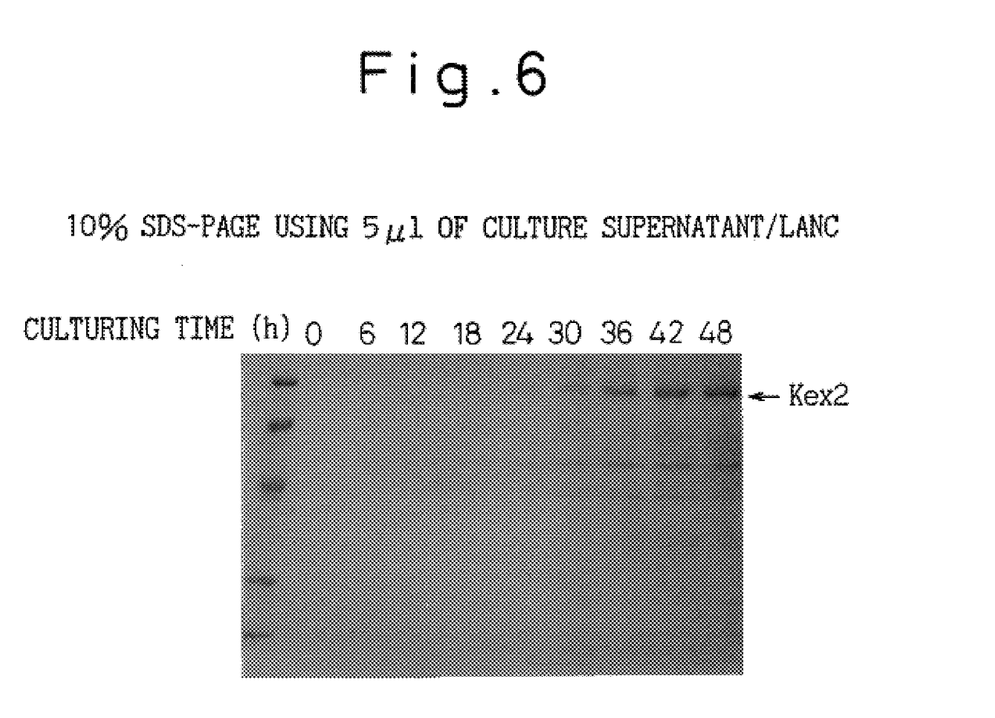
FIG. 6 is a photograph of an electrophoresis pattern that is the result of performing 10% SDS-PAGE on 5 $\mu$l of culture supernatant sampled at the indicated culturing times in culturing using a methanol addition rate of 4.5 ml/L-h.

During the time fluctuations in dissolved oxygen values were observed, in any condition, both of the cell density and the amount of secreted Kex2-660 produced increased (e.g., cell density and the amount of secreted Kex2-660 produced increased by about 2.5 times and about 7.4 times, respectively, during the time from the 24th to 48th hours after the start of culturing at a methanol addition rate of 4.5 ml/L.h; FIG. 5), and during the period in which methanol concentration in the culture medium was 0.1% (v/v) or less when fluctuations in dissolved oxygen values were observed that were synchronous with the methanol addition cycle, it was clear that the number of cells increased and Kex2-660 was expressed and secreted into the culture medium regardless the rate of methanol addition (FIGS. 5 and 6). Namely, it was found that the methanol addition rate at which the methanol concentration is the culture medium is 0.1% (v/v) or less and dissolved oxygen values fluctuate synchronously with the periodic addition of methanol is the suitable rate for cell growth and expression of the target product.

During culturing using methanol addition rates of 2.25 and 4.5 ml/L.h, the number of cells increased by 1400 times and 1800 times, respectively, at the 48th hour after the start of culturing, while 1260 MU and 2850 MU (equivalent to about 150 mg and 340 mg), respectively, of Kex2-660 were expressed and secreted per liter of culture supernatant (Table 1). Thus, it was clear that as long as methanol addition conditions are maintained such that periodic fluctuations in dissolved oxygen values continue (in other words, at a rate equal to or less than the maximum methanol consumption rate of the yeast), cell growth rate increases and the amount of Kex2-660 produced increases as the amount of methanol added increases.

Moreover, the time required for these cultures (48 hours) was short in comparison with the time (100–160 hours) for culturing divided into a growth phase, and production phase for methylotrophic yeasts deficient in enzymes of a methanol metabolic pathway, thus confirming the usefulness of the present invention.

FIG. 6 shows the results of SDS-PAGE performed in compliance with the method of Laemmli (Laemmli et al., Nature, 227, 680–685, 1970). Namely, 7 μl of 4x SDS sample buffer (375 mM Tris-HCl (pH 6.8), 30% (w/v) glycerol, 7% (w/v) SDS, 15% (v/v) 2-mercaptoethanol, 0.1% (w/v) bromphenol blue) were added to 20 μl of culture supernatant followed by heating for 5 minutes at 95° C. to prepare the SDS-PAGE sample. 6% SDS-PAGE was performed under conditions of 18 mA and 90 minutes using 7 μl of the above-mentioned sample. Following phoresis, the gel was stained with a staining solution (10% (v/v) acetic acid, 40% (v/v) methanol, 0.25% (w/v) Coumassie's brilliant blue R250). Those results are shown in FIG. 6.

3) Methanol Consumption Rate

During culturing using methanol addition rates of 2.25 and 4.5 ml/L.h, the methanol consumption rates per 1 g DCW of yeast (mean value every 6 hours) were determined (Table 2). The methanol consumption rate per liter of culture medium was taken to be the value resulting from subtracting the amount of methanol remaining from the amount of methanol added, while the yeast dry cell weight (DCW) was calculated by entering the OD600 value of the culture medium into a conversion formula determined in advance based on the relationship between the two.

Furthermore, since it was predicted that the effects of factors such as ventilation and heat generation caused by stirring would be significant in the case of a DCW of 0.5 g or less, this was eliminated from evaluation since there was a strong possibility that the correct amount of methanol consumption could not be calculated. During culturing of strain TK62 (pCU660) #10 based on periodic fluctuations in dissolved oxygen values, methanol consumption rates were determined to be 0.03–0.16 ml/gDCW-h when DCW was 0.5 g or more.

According to the present invention, the amount of methanol added that is suitable for both microorganism growth and expression of a heterogeneous gene controlled with a promoter can be determined from the amount of methanol consumed by microorganisms having a methanol metabolic pathway without measuring the concentration of methanol in the culture medium, in a heterogeneous gene expression system using a methanol-inducible promoter and a wild strain of microorganism having a methanol metabolic pathway for the host, without using a strain deficient in methanol metabolic pathway enzyme. In addition, during the time fluctuations in dissolved oxygen values synchronous with the periodic addition of methanol are observed when the methanol concentration in the culture medium is 0.1% (v/v) or less, the maximum rate of methanol consumption of the microorganisms is greater than or equal to the rate of methanol addition and the methanol does not accumulate in the culture medium, thereby enabling stable culturing in which the microorganisms are not destroyed by cell toxicity caused by the methanol.

Moreover, when the difference between the maximum rate of methanol consumption by the microorganisms and the methanol addition rate decrease so that the two are equal, since the fluctuation pattern of dissolved oxygen values changes, a suitable methanol addition rate for microorganism growth and expression of a heterogeneous gene controlled with a promoter can be determined and controlled using this change as an indicator. Since dissolved oxygen values are parameters that are normally used for control of culturing, and the methanol addition rate can be determined from their fluctuation pattern, methanol can be added according to an automatic feedback control loop which was not possible in the past in culturing of microorganisms having a methanol metabolic pathway.

Namely, the present invention provides a culturing method that is efficient both in terms of microorganism growth and production of the target product while also offering a high degree of reproducibility by maintaining the methanol addition rate equal to or less than the maximum methanol consumption rate of the microorganisms and near said maximum consumption rate (which enables powerful transcription to be induced from the promoter without inhibiting growth of the host). In addition, culturing of microorganisms having a methanol metabolic pathway that use methanol for their carbon source can be cultured rapidly and allow efficient production. Moreover, in the case of the gene product being secreted into the culture medium, the decreases in the amounts of methanol and glycerol contained in the culture medium can be expected to contribute to improved stability of the gene product and greater simplicity of the purification process.

What is claimed is:

1. A method for culturing microorganisms, said microorganisms having a methanol metabolic pathway and into which microorganisms an expression unit has been introduced wherein said expression unit comprises a target gene operably linked downstream from a promoter that can be induced by methanol; said method comprising:

culturing the microorganisms wherein methanol is added either periodically or continuously at the rate determined by following the step of:

determining a rate of addition of methanol to a culture of said microorganisms that is less than or equal to the maximum methanol consumption rate of said microorganisms wherein said addition is periodic and said rate causes the concentration of dissolved oxygen in the culture medium to fluctuate synchronously with the period of methanol addition, and wherein the induction of said promoter and the growth of the microorganisms occur simultaneously, and said promoter is induced by the addition of methanol at the rate determined.

2. A method according to claims 1 wherein during the period during which said concentration of dissolved oxygen fluctuates periodically, the methanol concentration in the culture medium is equal to or less than 0.1% (v/v).

3. A method according to claim 1 wherein the rate of methanol consumption when the cell density is a dry cell weight (DCW) of at least 0.5 g/liter is 0.01 to 0.20 ml/g DCW.h.

4. A method according to claim 1 wherein said promoter able to be induced by methanol is a promoter of an alcohol oxidase gene, a promoter of formic dehydrogenase gene or a promoter of a methanol oxidase gene.

5. A method according to claim 4 wherein said microorganism is *Candida boidinii*, and said promoter is a promoter of an alcohol oxidase gene of *Candida boidinii*.

6. A method according to claim 1 wherein said microorganisms are methylotrophic yeasts.

7. A method according to claim 6 wherein said methylotrophic yeasts are yeasts belonging to the genus Pichia, Hansenula or Candida.

8. A method according to claim 7 wherein said yeasts are the species *Pichia pastoris, Hansenula polymorpha* or *Candida boidinii*.

9. A method according to claim 1 wherein said target gene is a gene that codes for a protein.

10. A method according to claim 9 wherein said protein is an enzyme or other physiologically active substance.

11. A method according to claim 10 wherein said physiologically active substance is selected from the group consisting of growth hormone, growth hormone releasing hormone, adrenocorticotropic hormone (ACTH) releasing hormone, glucagon, glucagon-like peptide I, glucagon-like peptide II, Interferon α, Interferon β, Interferon γ, erythropoietin (EPO), thrombopoietin (TPO), granulocyte colony-stimulating factor (G-CSF), hepatocyte growth factor (HGF), tissue plasminogen activator (tPA), stem cell factor, and TGF.

12. A method according to claim 10 wherein said enzyme is selected from the group consisting of Kex2 protease, secretary Kex2 protease, prohormone convertase ⅓ (PCI/3), prohormone convertase 2 (PC2), furin, peptide C-terminal α-amidase, staphylococcal protease V8, achromobacter protease I (API), placental leucine aminopeptidase, and cytoplasmic platelet activating factor acetylhydrase.

13. A method according to claim 12 wherein said secretory of Kex2 protease is secreted in a culture medium.

14. A method according to claim 12, wherein the secretory Kex 2 protease is Kex 2-660.

15. A method for culturing microorganisms, said microorganisms having a methanol metabolic pathway and into which microorganisms an expression unit has been introduced wherein said expression unit comprises a target gene operably linked downstream from a promoter that can be induced by methanol; said method comprising:

a) determining a rate of addition of methanol to a culture of said microorganisms that is less than or equal to the maximum methanol consumption rate of said microorganisms wherein said addition is periodic and said rate causes the concentration of dissolved oxygen in the culture medium to fluctuate synchronously with the period of methanol addition, and wherein the induction of said promoter and the growth of the microorganisms occur simultaneously, and said promoter is induced by the addition of methanol at the rate determined; and b) culturing said microorganisms under th conditions determined in step (a).

16. A method according to claim 15 wherein during the period during which said concentration of dissolved oxygen fluctuates synchronously, the methanol concentration in the culture medium is equal to or less than 0.1% (v/v).

17. A method according to claim 15 wherein the rate of methanol consumption when the cell density is a dry cell weight (DCW) of at least 0.5 g/liter is 0.01 to 0.20 ml/g DCW.h.

18. A method according to claim 15 wherein said promoter able to be induced by methanol is a promoter of an alcohol oxidase gene, a promoter of formic dehydrogenase gene or a promoter of a methanol oxidase gene.

19. A method according to claim 18 wherein said microorganism is *Candida boidinii*, and said promoter is a promoter of an alcohol oxidase gene of *Candida boidinii*.

20. A method according to claim 15 wherein said microorganisms are methylotrophic yeasts.

21. A method according to claim 20 wherein said methylotrophic yeasts are yeasts belonging to the genus *Pichia, Hansenula* or *Candida*.

22. A method according to claim 21 wherein said yeasts are *Pichia pastoris, Hansenula polymorpha* or *Candida boidinii*.

23. A method according to claim 15 wherein said target gene is a gene that codes for a protein.

24. A method according to claim 23 wherein said protein is an enzyme or other physiologically active substance.

25. A method according to claim 24 wherein said physiologically active substance is selected from the group consisting of growth hormone, growth hormone releasing hormone, adrenocorticotropic hormone (ACTH) releasing hormone, glucagon, glucagon-like peptide I, glucagon-like peptide II, Interferon α, Interferon β, Interferon γ, erythropoietin (EPO), thrombopoietin (TPO), granulocyte colony-stimulating factor (G-CSF), hepatocyte growth factor, tissue plasminogen activator (tPA), stem cell factor, and TGF.

26. A method according to claim 24 where in said enzyme is selected from the group consisting of Kex2 protease, secretary Kex2 protease, prohormone convertase ⅓ (PCI/3), prohormone convertase 2 (PC2), furin, peptide C terminal α-midase, staphylococcal protease V8, achromobacter protease I (API), placental leucine aminopeptidase, and cytoplasmic platelet activating factor acetylhydrase.

27. A method according to claim 26 wherein said secretary Kex2 protease is secreted in a culture medium.

28. A method according to claim 26, wherein the secretory Kex 2 protease is Kex 2-660.

* * * * *